United States Patent
Bartel et al.

(10) Patent No.: US 8,178,858 B2
(45) Date of Patent: May 15, 2012

(54) DEVICE AND METHOD FOR ALTERING THE CHARACTERISTICS OF THREE-DIMENSIONAL SHAPED PARTS USING ELECTRONS AND USE OF SAID METHOD

(75) Inventors: Rainer Bartel, Dresden (DE); Volker Kirchhoff, Wehlen (DE); Goesta Mattausch, Ullersdorf (DE); Olaf Roeder, Dresden (DE); Joerg Kubusch, Dresden (DE)

(73) Assignee: Fraunhofer-Gesellschaft zur Foerderung der Andgewandten Forschung E.V., Munich (DE)

( * ) Notice: Subject to any disclaimer, the term of this patent is extended or adjusted under 35 U.S.C. 154(b) by 458 days.

(21) Appl. No.: 12/293,756

(22) PCT Filed: Mar. 20, 2007

(86) PCT No.: PCT/EP2007/002458
§ 371 (c)(1),
(2), (4) Date: Sep. 19, 2008

(87) PCT Pub. No.: WO2007/107331
PCT Pub. Date: Sep. 27, 2007

(65) Prior Publication Data
US 2009/0184262 A1 Jul. 23, 2009

(30) Foreign Application Priority Data
Mar. 20, 2006 (DE) .................. 10 2006 012 668

(51) Int. Cl.
*A61N 5/00* (2006.01)
(52) U.S. Cl. ............. 250/492.3; 250/492.1; 219/121.29; 219/121.12
(58) Field of Classification Search .................. None
See application file for complete search history.

(56) References Cited

U.S. PATENT DOCUMENTS

| | | | | |
|---|---|---|---|---|
| 2,741,704 | A | | 4/1956 | Trump et al. |
| 3,624,391 | A | * | 11/1971 | Davison ................. 250/453.11 |
| 3,749,967 | A | * | 7/1973 | Douglas-Hamilton et al. 315/85 |
| 3,901,807 | A | * | 8/1975 | Trump ..................... 210/198.1 |
| 4,121,086 | A | | 10/1978 | Auslender et al. |

(Continued)

FOREIGN PATENT DOCUMENTS
DE 27 20 514 A1 11/1977
(Continued)

OTHER PUBLICATIONS

Schiller, Panzer, Heisig: Elektronenstrahitechnologie, Wiss. Verlagsgesellschaft Stuttgart 1977, S. 101-108.

(Continued)

*Primary Examiner* — Jack Berman
*Assistant Examiner* — Andrew Smyth
(74) *Attorney, Agent, or Firm* — Greenblum & Bernstein, P.L.C.

(57) ABSTRACT

The invention relates to a device and a method for altering the characteristics of a three-dimensional article by means of electrons, including at least one electron accelerator for generating accelerated electrons and two electron exit windows, wherein the two electron exit windows are arranged opposite one another, wherein the two electron exit windows and at least one reflector delimit a process chamber in which the surface or surface layer of the article are bombarded with electrons, wherein an energy density distribution inside the process chamber can be detected at least over one spatial dimension by means of a sensor system.

30 Claims, 3 Drawing Sheets

U.S. PATENT DOCUMENTS

| | | | | |
|---|---|---|---|---|
| 4,252,413 A * | 2/1981 | Nablo | | 250/310 |
| 4,352,672 A * | 10/1982 | Spiess et al. | | 8/444 |
| 4,362,965 A * | 12/1982 | Kendall | | 313/420 |
| 4,496,881 A * | 1/1985 | Cheever | | 315/357 |
| 4,543,487 A | 9/1985 | Puumalainen et al. | | |
| 4,721,967 A * | 1/1988 | Roche | | 347/227 |
| 4,724,059 A | 2/1988 | Collier | | |
| 4,829,190 A * | 5/1989 | Okamoto et al. | | 250/492.3 |
| 4,944,132 A * | 7/1990 | Carlsson et al. | | 53/167 |
| 4,959,550 A * | 9/1990 | Kashiwagi et al. | | 250/492.3 |
| 4,983,849 A * | 1/1991 | Thompson et al. | | 250/492.3 |
| 5,004,926 A * | 4/1991 | Vassenaix et al. | | 250/492.3 |
| 5,391,958 A | 2/1995 | Kelly | | |
| 5,414,267 A | 5/1995 | Wakalopulos | | |
| 5,631,471 A * | 5/1997 | Anderl et al. | | 250/492.3 |
| 5,635,714 A * | 6/1997 | Nablo et al. | | 250/305 |
| 5,801,387 A * | 9/1998 | Nablo et al. | | 250/492.3 |
| 5,825,037 A * | 10/1998 | Nablo | | 250/492.3 |
| 6,078,046 A * | 6/2000 | Mori et al. | | 250/311 |
| 6,617,596 B1 | 9/2003 | Korenev | | |
| 6,623,706 B2 * | 9/2003 | Avnery | | 422/186 |
| 6,696,018 B2 * | 2/2004 | Buchanan | | 422/22 |
| 6,738,451 B2 * | 5/2004 | Avnery | | 378/64 |
| 6,833,551 B2 * | 12/2004 | Avnery | | 250/492.3 |
| 6,897,620 B1 * | 5/2005 | Takeuchi et al. | | 315/169.3 |
| 7,187,114 B2 * | 3/2007 | Takeuchi et al. | | 313/495 |
| 7,189,978 B2 * | 3/2007 | Avnery | | 250/455.11 |
| 7,323,137 B2 * | 1/2008 | Avnery | | 422/24 |
| 7,544,269 B2 * | 6/2009 | Strang | | 156/345.24 |
| 7,749,434 B2 * | 7/2010 | Naslund et al. | | 422/1 |
| 2002/0011405 A1 * | 1/2002 | Avnery | | 204/158.2 |
| 2002/0149321 A1 * | 10/2002 | Avnery | | 315/169.3 |
| 2003/0091468 A1 * | 5/2003 | Buchanan | | 422/22 |
| 2004/0060811 A1 * | 4/2004 | Avnery | | 204/157.3 |
| 2004/0104684 A1 * | 6/2004 | Takeuchi et al. | | 315/169.1 |
| 2005/0031077 A1 * | 2/2005 | Avnery | | 378/64 |
| 2006/0076507 A1 * | 4/2006 | Avnery | | 250/454.11 |
| 2006/0159583 A1 * | 7/2006 | Naslund et al. | | 422/22 |
| 2007/0090303 A1 * | 4/2007 | Kristiansson et al. | | 250/492.3 |
| 2007/0114432 A1 * | 5/2007 | Kristiansson et al. | | 250/397 |
| 2007/0145304 A1 | 6/2007 | Roche et al. | | |
| 2007/0158539 A1 * | 7/2007 | Zavadlsev et al. | | 250/251 |
| 2008/0267354 A1 * | 10/2008 | Holm et al. | | 378/122 |
| 2009/0173039 A1 * | 7/2009 | Slomski et al. | | 53/167 |
| 2010/0270197 A1 * | 10/2010 | Porret et al. | | 206/459.1 |

FOREIGN PATENT DOCUMENTS

| | | |
|---|---|---|
| DE | 34 16 198 A1 | 11/1984 |
| DE | 19518623 A1 * | 11/1996 |
| DE | 198 16 246 C1 | 12/1999 |
| DE | 199 42 142 A1 | 3/2001 |
| WO | WO-94/28573 A1 | 12/1994 |
| WO | WO-99/39750 A1 | 8/1999 |
| WO | WO-99/39751 A1 | 8/1999 |
| WO | WO-02/061464 A1 | 8/2002 |
| WO | WO-02/075747 A2 | 9/2002 |
| WO | WO-2005/041241 A1 | 5/2005 |
| WO | WO-2007/107201 A1 | 9/2007 |

OTHER PUBLICATIONS

Office action of priority application DE 10 2006 012 668.8-54, with English language translation, 2007.

* cited by examiner (with density $\rho = 1000$ g/m$^3$ corresponds to the penetration depth in mm)

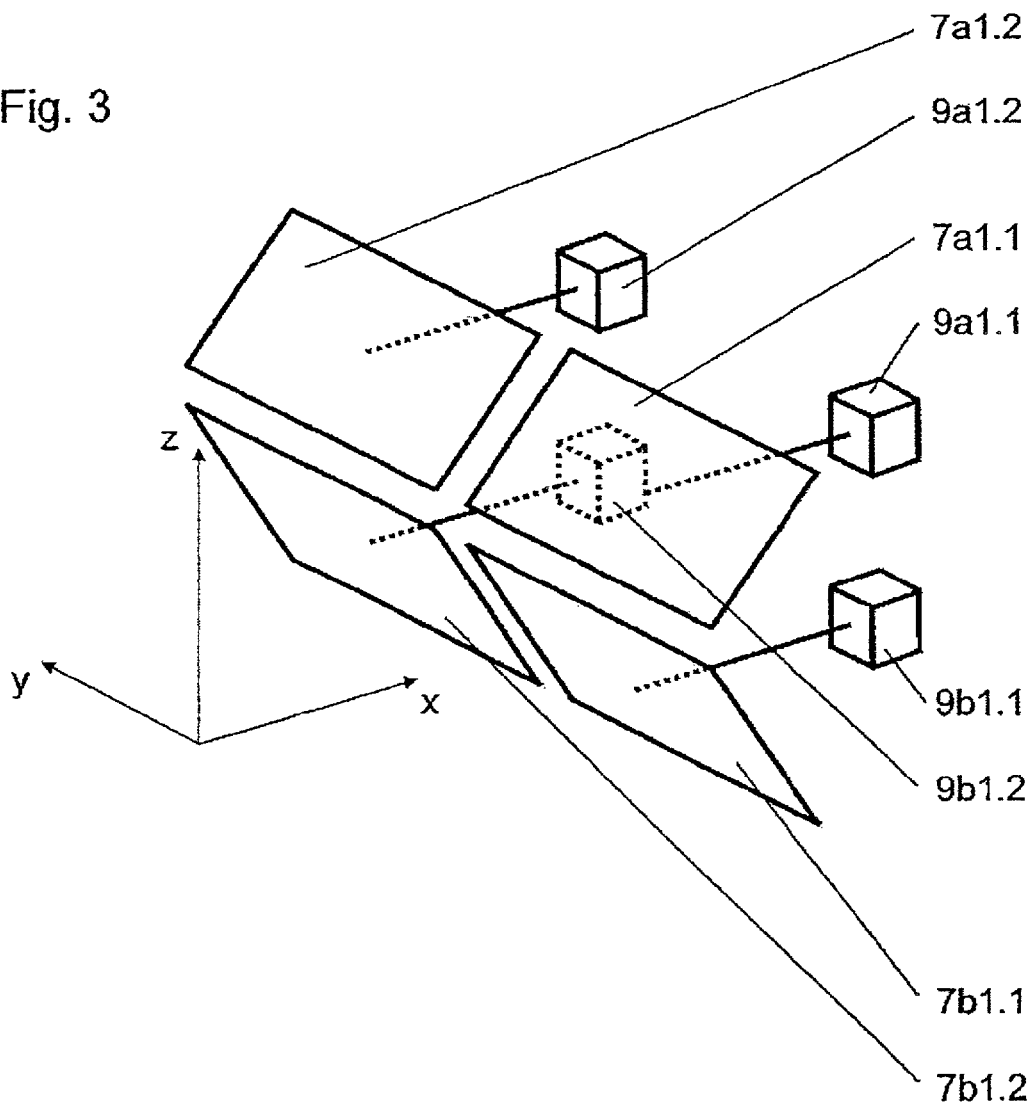

DEVICE AND METHOD FOR ALTERING THE CHARACTERISTICS OF THREE-DIMENSIONAL SHAPED PARTS USING ELECTRONS AND USE OF SAID METHOD

CROSS-REFERENCE TO RELATED APPLICATIONS

This application claims priority under 35 U.S.C. §119 of German Patent Application No. 10 2006 012 668.8-54, filed on Mar. 20, 2006.

This application is a national phase of international application PCT/EP2007/002458, which international application was filed on Apr. 4, 2007.

BACKGROUND OF THE INVENTION

Field of the Invention

The invention relates to a device and a method for modifying material characteristics on the surface and in the surface area of three-dimensional articles, such as molded parts, using the energy of electrons. Furthermore, uses of the method are shown.

Using electrons, energy can be fed into materials in a spatially and chronologically determinate manner in order to alter their material characteristics on the surface, in the surface layer or in the volume. The electrons required to this end are generated, formed and accelerated in electron accelerators before they are guided via a usually flat electron exit window out of the high vacuum to a higher pressure level in the process chamber. A constant electron density over the entire extent of the electron exit window is usually desirable thereby. After the penetration of the gas layer (for example, air) in the distance between electron exit window and product, the electrons reach the product surface to be treated.

Shaped beam generators, also called band emitters, or axial-beam generators are used as electron accelerators. An electron accelerator according to the prior art embodied as an axial-beam generator comprises in addition an electron beam deflection chamber with a beam deflection system, by means of which a generated electron beam is periodically deflected over the entire electron exit window and with virtually the same dwell time on time average in all partial areas of the window.

Three-dimensional parts or articles, such as, e.g., packaging, medical implants, surgical instruments, prostheses of different materials (e.g., plastic, paper, metal, ceramics) are used in various fields (for example, the packaging industry, pharmaceuticals, medical engineering, plastics industry). For certain uses, an alteration of properties (for example, sterilization, surface functionalizing, cross-linking, hardening) of the entire surface and the surface area of the article is necessary.

It is known to influence characteristics of the entire surface of three-dimensional articles by means of electron energy, in that an article is guided past an electron exit window in several passes (DE 199 42 142 A1) and in an altered position. Known devices for generating electrons for the modification of article characteristics are embodied such that a virtually identical electron energy density is generated and emitted over the entire electron exit window.

The alteration of the position of a article ensures that the entire article surface is bombarded with electron energy. One disadvantage of devices of this kind is that a multiple pass is associated with a relatively high expenditure of time. Altering the position of the article between the individual passes cannot be carried out in an arbitrary manner, either, but must be coordinated such that individual surface areas in total are not bombarded with different electron energy densities, which would lead to different characteristics.

According to the prior art, the entire surface of a three-dimensional article is modified during only one pass by means of electron energy, in that several (at least two or three) electron exit windows are arranged such that they surround the cross section of an article, wherein the article is guided through between these electron exit windows and thus the entire three- dimensional surface is bombarded with electrons.

A device for sterilizing the surface of articles by means of electron energy is known from LINAC Technologies (technical description "ELECTRON BEAM SURFACE STERILISATION SYSTEM 200 KeV—The Ke VAC S"), in which three electron accelerators are arranged such that their associated electron exit windows surround a volume with the cross section of an isosceles triangle, through which the articles to be sterilized are guided through in one pass. Although with devices of this type the time expenditure is reduced with respect to known solutions in which an article is bombarded with electrons in several passes, the technical expenditure is very great due to the use of three electron accelerators.

Similar arrangements of three electron exit windows are known in which the electrons are generated, however, only by means of one electron accelerator and are distributed among the three electron exit windows with the aid of a deflection system.

All known solutions with three electron exit windows utilize the advantage that through their triangular arrangement the electron accelerators do not influence one another reciprocally or do so only to a negligible extent, that is, that the accelerated electrons of an electron accelerator do not emit substantial energy fractions to the respectively other electron accelerators. This is necessary in order to limit the energy fraction absorbed in the electron exit window and thus its operating temperature to a subcritical level. If the material application temperature is exceeded, the sensitive material of the window covering would otherwise be destroyed by the mechanical stress of the atmospheric pressure applied from outside, relative to the high vacuum in the interior of the beam generator. A maximum temperature of approximately 400° C. must not be exceeded on any account for the titanium film conventionally used in electron exit windows. A maximum of 200-250° C. is assumed for continuous operation.

The arrangement of only two opposite electron exit windows is likewise known. With the technologically necessary small distance between the electron exit windows, a considerable energy fraction is thereby inserted into the opposite electron exit window, which results in a temperature increase by a factor of 2 to 5, depending on the construction. The necessary limitation of the maximum temperature can be achieved only by proportional limitation of the beam current. However, this limits the effectiveness of the total system.

Another possibility for limiting the temperature of two opposite electron exit windows is the arrangement of an additional absorber such as, e.g., an (at least partially transparent) transport belt between the electron exit windows (U.S. Pat. No. 2,741,704). A substantial energy fraction is then allocated to the absorber, which limits the irradiation of additional energy on the opposite electron exit window.

The solution is likewise known of arranging two electron exit windows opposite one another and laterally offset in the product transport direction. The radiation of power into the respectively opposite electron accelerator and thus its overheating are thus prevented.

With the known devices, in which two and more electron exit windows surround an article and in which a virtually identical electron energy density is emitted over an entire electron exit window and an article is bombarded with electrons in only one pass, individual surface partial areas of the article, depending on the geometry thereof and the resulting differing distance of the surface partial areas from an electron exit window, can be bombarded with a different dose (energy per unit surface area or energy per mass unit) of electron energy.

In order to realize a certain characteristic on an article, a certain dose of electron energy is necessary. Expediently, the output of the electron generator is adjusted such that on those surface areas at which the lowest dose arrives, the dose arriving there corresponds exactly or corresponds at least to the dose that is necessary for the modification of the characteristic. All other surface areas of the article are inevitably bombarded with an increased dose. This increased dose of energy is also called an overdose. The higher the overdose in individual areas of an article, the more marked the deviation of the characteristics in these areas from the target parameters. However, an overdose of electron energy not only has a negative impact on the characteristics to be modified of an article, but can also lead to undesirable side effects that may even be damaging to the process through the formation of undesirable by-products (for example, ozone) in the process gas (for example, air).

A parameter described as an overdose factor indicates the factor by which a necessary dose for adjusting a desired characteristic is exceeded. With the known devices, depending on the geometry of articles to be modified, overdose factors are reached in individual surface areas that are not acceptable for many uses in order to realize sufficiently uniform characteristics over the entire surface and which also entails the already cited undesirable side effects.

To achieve high productivities, an adjusted high transport speed of the articles is necessary. Due to the proportionality of transport speed and beam current, the achievement of a technologically predetermined minimum dose (for the application area of sterilization, this is, e.g., 25 kGy) necessitates an increase of the beam current proportional to the speed, which leads to the disproportionate increase of the operating temperature of the electron exit windows. In the case of the arrangement of two electron accelerators opposite one another without additional absorbers or lateral displacement of the systems, no solution suitable for practical use currently exists.

SUMMARY OF THE INVENTION

The invention is therefore based on the technical problem of creating a device and a method by means of which the disadvantages of the prior art are overcome. In particular, the device and method should be suitable for modifying characteristics of three-dimensional articles with a low expenditure in terms of time and technology such that a sufficiently uniform modification of the entire surface or of a surface layer of the articles is carried out and nevertheless have none of the disadvantages limiting productivity from the overall arrangement of the electron accelerators. The overdose factor should be so low thereby that it corresponds to the technical/technological requirements of the articles.

According to the prior art, it was hitherto assumed that at least two electron exit windows with lateral displacement or with an absorber located between them or with limited beam current or three electron exit windows are necessary in order to be able to bombard the cross-sectional circumference of a three-dimensional article in one pass completely with electrons and to produce the desired changes in characteristics. It is shown according to the invention that a limitation of the beam current resulting from an arrangement of electron exit windows opposite one another is not necessary and in addition a bombardment of an article surface with a virtually uniformly distributed energy dose is possible.

A device according to the invention for altering characteristics of a three-dimensional article using electrons comprises at least one electron accelerator for generating accelerated electrons and two electron exit windows, and only two electron exit windows, wherein the two electron exit windows are arranged opposite one another. Jointly with at least one reflector, the two electron exit windows delimit a process chamber in which the article is bombarded with electrons. The electron exit windows are thereby arranged so far apart from one another that an influence of an electron exit window by the emitted energy of the electron exit window lying opposite is negligible. The distance necessary for this is essentially dependent on the acceleration voltage of the electrons, the thickness and density of the film of an electron exit window and the density of the gas between the electron exit windows.

The disadvantage that all surface areas (in particular the areas that run largely perpendicular to the surface of the electron exit windows) of the article to be modified are no longer bombarded sufficiently with electrons with a distance of this type, is offset in that the reflector is shaped and arranged such that electrons (in particular from the surface areas of the electron exit windows) which would not strike the article, are reflected by the reflector onto the surface areas of the article that exhibit a deficit in the bombardment with electrons.

Furthermore, a device according to the invention comprises a sensor system by means of which the energy density distribution in the process chamber can be detected over at least one spatial dimension. Depending on the data detected hereby, the energy density emitted via the electron exit windows can then be controlled such that a uniform bombardment with electrons on the article surface takes place within the dimension in which the energy density distribution was detected.

A device of this type is particularly suitable for articles that have a largely round, oval or trapezoidal cross section. However, articles with a differently shaped cross section can also be modified therewith.

To generate the accelerated electrons, an electron accelerator can be used by which the electrons are distributed among the two electron exit windows with a corresponding deflection control. Alternatively, however, a separate electron accelerator can also be assigned to each electron exit window. Area accelerators, also called band emitters, as well as axial beam generators are suitable as electron accelerators.

With a parallel alignment of two opposite electron exit windows embodied in a flat manner with optimum spacing and arrangement according to the invention of a reflector system, it was possible to realize overdose factors below the value 4 during the electron treatment of articles with largely trapezoidal cross section, whereas with the treatment of identical articles in devices according to the prior art with three electron exit windows or with two electron exit windows lying opposite one another and an absorber lying between them, overdose factors of far more than 4 had to be accepted. Compared with known solutions, thus with high productivity on the one hand energy is saved and on the other hand the surface of the three-dimensional product is protected from radiation-chemical damage and side effects damaging to the process are reduced due to the lower discharge of ozone.

One embodiment of the invention comprises two reflectors that delimit the process chamber and are arranged opposite one another in a mirror symmetrical manner. Each of the two reflectors can thereby comprise a plurality of partial reflectors.

In a particular embodiment, the reflectors are at the same time a component part of the sensor system for detecting an energy density distribution. Hereby, for example, a number of reflectors or partial reflectors that, in such an embodiment, can comprise a material with high atomic number (for example, gold, tungsten or molybdenum) can be connected electrically via a resistor with the electric mass or another electric potential. Electrons that are not reflected by a reflector/partial reflector then form a beam current so that a voltage can be detected via a resistor belonging to the reflector/partial reflector. A corresponding statement can then also be made using the values of the detected voltage at the individual reflectors/partial reflectors regarding the energy density of the electrons reflected by a reflector and corresponding control steps can be taken regarding a uniform energy density distribution.

It is particularly advantageous if the energy density distributions are detected and correspondingly evaluated in this manner in the x, y and z direction of a Cartesian coordinate system.

With the aid of a combination of this type of reflectors and sensor system, for example, it can also be detected whether a article is located in the process chamber. The generation of electrons can be controlled depending thereon, so that the output of the electron accelerators is adjusted to a process-specific value, for example, when an article is located in the process chamber, and otherwise is lowered or reduced to zero.

With a device according to the invention the maximum occurring overdose factor or a uniform bombardment with electrons of the article surface can be further optimized in that the two electron exit windows are aligned to one another at an angle depending on the geometry of an article to be treated such that as many surface sections of the article as possible are spaced apart with virtually the same measurement from the respectively energy-emitting electron exit window.

In addition to flat shaped electron exit windows, these can also be embodied, for example, in a concave manner towards the article or also adapted to the geometry of the article, which likewise causes as many surface sections of the article as possible to be spaced apart by virtually the same measurement from the respective energy-emitting electron exit window, whereby lower overdose factors can be achieved.

With one embodiment an electron generator comprises a device by means of which the electron energy density emitted over the area of at least one electron exit window is controllable such that different electron energy densities are emitted over individual partial areas of the electron exit window. Thus, for example, in the partial areas of the window in which surface areas of an article lie opposite the window at a great distance, the electron energy density can be increased with respect to partial areas of the window in which surface areas of the article lie opposite the window at a small distance, so that as far as possible all the surface areas of the article absorb the same dose and thus uniform characteristics are formed over the entire surface in the processing depth to be modified (surface or surface layer). Constructive systems lying within a shaped beam generator (without electromagnetic beam deflection), engaging in the electron optics, such as apertures, compensation electrodes or components influencing the temperature of the cathodes, which systems influence the distribution of the electron current, can be used as a means of modifying the electron energy density over individual partial areas of an electron exit window.

Another possibility lies in the arrangement of means outside the electron accelerator, in particular of magnetic and/or electric systems that influence the direction of the accelerated electrons.

Another embodiment of the invention is characterized in that at least one electron exit window is arranged in a movable manner. For example, at the beginning when an article is inserted in the process chamber between two windows, this electron exit window can thus be tilted toward the front face of the article in order to improve the bombardment with electrons at the front face. During the further transport of the article through the process chamber, the window can then be tilted in the direction of parallel alignment to the opposite window and when leaving the process chamber in the direction of the rear of the article. However, it is also possible for other movement forms to be carried out with the window. For example, the window thus can be carried along for a time in the movement direction of the article.

Another optimization in the object of modifying the characteristics uniformly over the entire surface of an article, is possible by means of a device that controls via magnetic and/or electric deflection systems not only the point at which an electron leaves an electron exit window, but also the exit direction of the electron at this point. Certain surface areas of the article can thus be bombarded with electrons in an even more targeted manner.

In a particular embodiment, at least one electron exit window is embodied as a vacuum-tight film and thus as a pressure barrier between beam guide chamber and process chamber. Alternatively, an electron exit window can also be embodied as a gas-permeable pressure stage arrangement between the electron generator and process chamber.

A method according to the invention for altering characteristics of a three-dimensional article by means of electrons is characterized in that electrons are generated, accelerated and emitted over the surface of two electron exit windows lying opposite one another by means of at least one electron accelerator, wherein the two electron exit windows and at least one electron reflector delimit a process chamber in which the surface or an surface layer of the article is bombarded with electrons, wherein an energy density distribution within the process chamber is detected over at least one spatial dimension by means of a sensor system and the spacing of the electron exit windows is adjusted such that an influence of an electron exit window by the emitted energy of the electron exit window lying opposite is negligible.

Advantageously, the spacing of the electron exit windows is adjusted depending on the acceleration voltage of the electrons and the thickness and the density of the electron exit windows.

With one embodiment, the spacing a of the electron exit windows is adjusted in a range that results from the formula:

$$a = f * \frac{6{,}67 * 10^{-7} \frac{(U_b * k_1)^{5/3}}{\rho_W} * k_2 - \rho_F * d_F}{\rho_G}$$

whereby,
a=spacing of the electron accelerators
$U_b$=acceleration voltage
$\rho_W$=density of water $\rho_G$=density of the medium between the electron exit windows
$\rho_F$=density of the window film
$d_F$=thickness of the window film
$k_1$=1*V$^{-1}$
$k_2$=1*(g/m$^2$)$^{-1}$
f=spacing factor (0.5<f<1.5).

The range for the spacing a results hereby from the value range of the spacing factor f, wherein an optimum computing value for the spacing a results from a spacing factor with a value of 1.

Different alternative possibilities are available for the irradiation of an article inside the process chamber between the two electron exit windows.

Thus, an article can be guided through the process chamber at constant speed and during this can be bombarded with electrons.

Alternatively, there is also the possibility that an article is guided into the process chamber and there in the stationary state is bombarded with electrons by a one-time or multiple irradiation operation.

In a further alternative embodiment an article is bombarded with electrons in the so-called step-and-repeat mode. This means that the article is guided into the process chamber such that at least one piece of the article projects into the process chamber. In the stationary state the article is then bombarded with electrons from the electron exit windows. This is followed by another transport step in which the article is moved another distance into or through the process chamber. In the stationary state an irradiation step is then again carried out in which the article is again bombarded with electrons. Transport and irradiation steps thus alternate until the article has been moved completely through the process area. A respective transport step can be carried out thereby such that the individual surface areas that are bombarded with electrons after the respective transport steps are adjacent to one another or overlap one another with an alternative variant.

Finally, a modification of an article can also be carried out in that the article in the process chamber rotates around an axis extending between the two electron exit windows and during this is bombarded with electrons through a one-time or multiple irradiation operation.

Methods according to the invention can be used, for example, for sterilizing packaging and products of the pharmaceutical industry and medical engineering, for the sterilization/disinfecting or degerming of products such as fruits, eggs or other natural products, for the modification of plastics, hardening of coatings or for sterilizing/disinfecting objects.

BRIEF DESCRIPTION OF THE DRAWINGS

The invention is described in more detail below based on an exemplary embodiment. The drawings show:

FIG. 3 A diagrammatic representation of a sensor system, comprising the reflectors 7a1 and 7b1 from FIG. 1.

DETAILED DESCRIPTION OF THE INVENTION

Figure 1:
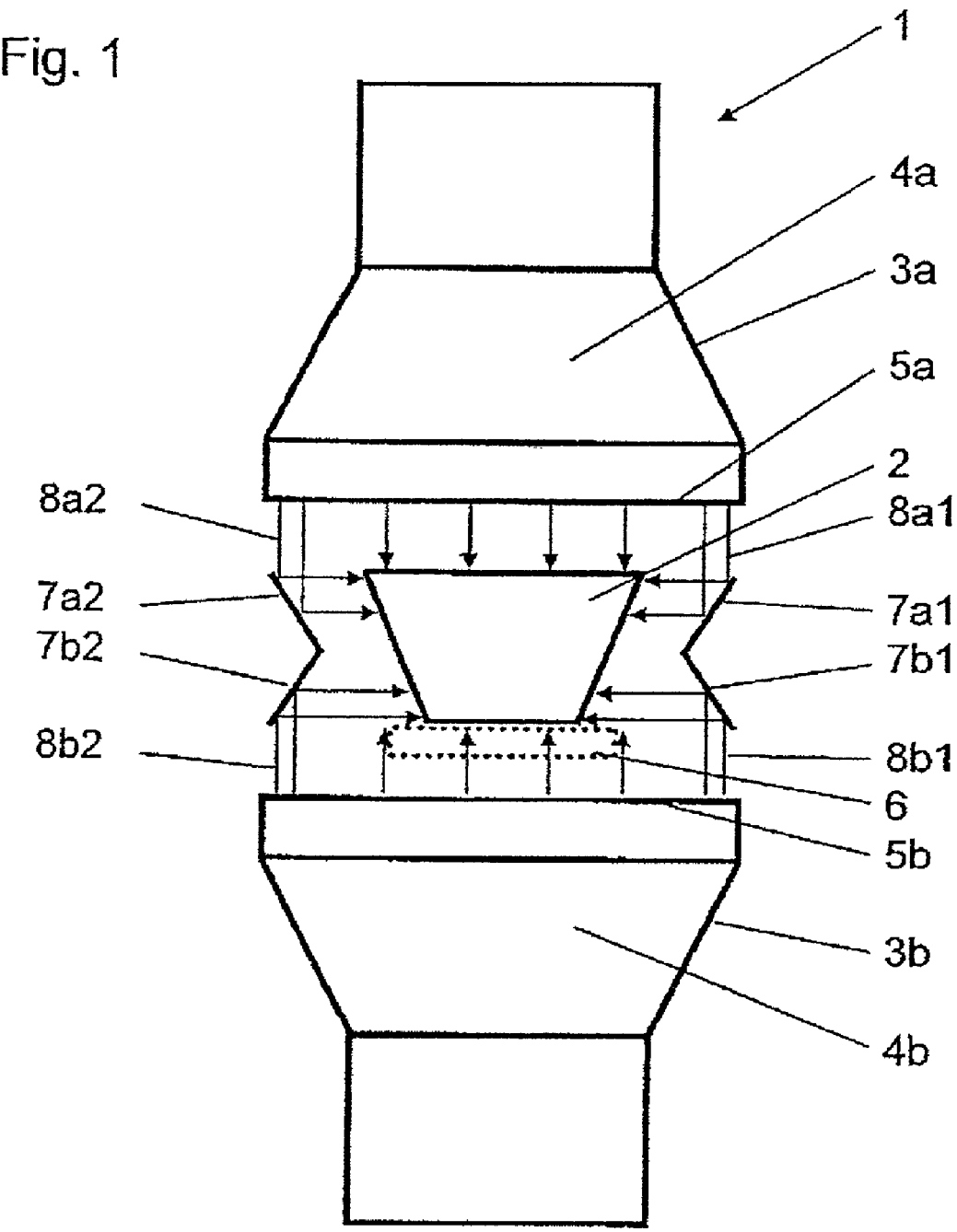
FIG. 1 A diagrammatic cross-sectional representation of a device according to the invention.

In FIG. 1 a device 1 for electron treatment for the purpose of sterilizing the surface of an article 2 is shown diagrammatically in cross section. Article 2 is an elongated object with a trapezoidal cross section. Device 1 comprises two electron accelerators 3a, 3b embodied as shaped beam generators 3a, 3b that respectively comprise an electron acceleration chamber 4a, 4b and an electron exit window 5a, 5b. The electron exit windows are hereby embodied as a titanium film 11 μm thick. The electron accelerators 3a, 3b are arranged such that the flat shaped electron exit windows 5a, 5b are aligned parallel opposite one another. Article 2 is guided continuously through between the two electron exit windows 5a, 5b on a conveyor belt system 6 interrupted in the area of the electron exit window 5b and shown by a dotted line in FIG. 1 and the entire surface thereof is thereby bombarded with electron energy. Respectively, the lowest energy dose is thereby transferred to the oblique lateral surfaces of the article 2 at the points furthest distant from the electron exit windows, which is compensated by the arrangement of electron reflectors 7a1, 7b1, 7a2, 7b2 of gold. This is carried out in that the unused edge beams 8a1, 8a2, 8b1, 8b2 of the respective electron beam of the two electron accelerators 3a, 3b strike the respectively closest electron reflector, are reflected there and guided to the article through the angled arrangement of the reflectors in the range of the lowest dose. An overall arrangement of this type results in an energy dose on the entire surface or else in an surface layer of the article with a minimum overdose factor, a maximum utilization of the electron current and a minimum of the reactive ozone occurring in the air gap.

The spacing of the two electron exit windows 5a and 5b selected in the arrangement corresponds largely to the following context:

$$a = f * \frac{6{,}67 * 10^{-7} \frac{(Ub * k_1)^{5/3}}{\rho_W} * k_2 - \rho_F * d_F}{\rho_G}$$

whereby,
a=spacing of the electron accelerators
$U_b$=acceleration voltage
$\rho_W$=density of water
$\rho_G$=density of the medium between the electron exit windows
$\rho_F$=density of the window film
$d_F$=thickness of the window film
$k_1$=1*V$^{-1}$
$k_2$=1*(g/m$^2$)$^{-1}$
f=spacing factor (0.5<f<1.5), wherein f=1 defines an optimum spacing.

With titanium films 11 pm thick as electron exit windows 5a, 5b and the medium air (here assumed 1188 g/m$^3$) between these electron exit windows an optimal spacing results of 196 mm.

Figure 2:
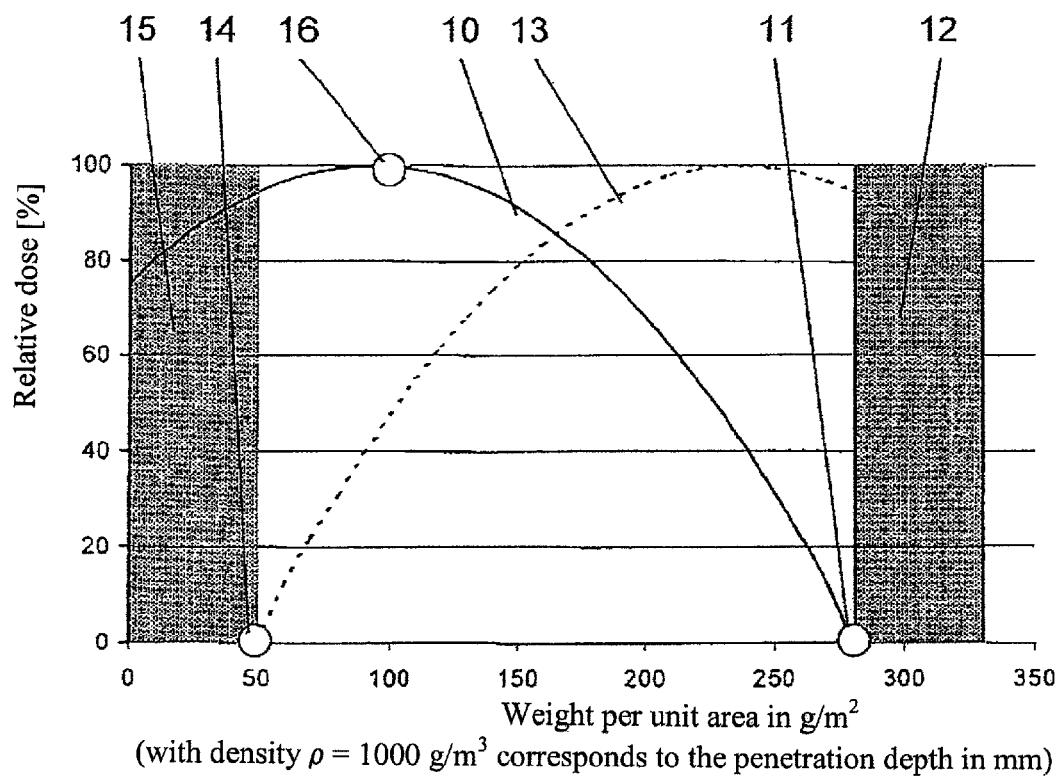
FIG. 2 A graphic representation of the depth dose distribution of the electrons emitted from the electron exit windows 5a and 5b from FIG. 1 lying opposite one another.

FIG. 2 shows by way of example the depth dose distribution of the arrangement according to the invention of two electron accelerators according to FIG. 1 with a thickness of the electron exit window films (titanium) of 11 μm with an acceleration voltage of 150 kV and an optimum spacing of the electron exit windows of 196 mm. Curve 10 represents the distribution of the energy dose generated by electron accelerator 3a over the penetration depth of the electrons. The energy of the electrons has dropped to zero at point 11 with a weight per unit area of 280 g/m$^2$ (with a density of 1000 g/m$^3$ corresponding to a penetration depth in mm compliant with the numerical value—in the given case therefore 280 mm). Only at this distance is the electron exit window 5b located, the weight per unit area of which is shown as a shaded area in FIG. 2. The same conditions result for the electron accelerator 3b, the generated energy dose of which shown as curve 13 is reduced to zero at point 14 (in the representation FIG. 2 at approximately 50 g/m$^2$). The distance of the points 11 and 14 represents the distance between the two electron exit windows 5a and 5b and corresponds to the weight per unit area of approximately 230 g/m$^2$, which multiplied by the density of air (here assumed at 1188 g/m$^3$) corresponds to approximately 196 mm. According to the invention under the assumed conditions an optimal spacing of 196 mm therefore results, at which no power is absorbed in the respectively opposite electron exit window. The distance can be varied according to the spacing factor.

FIG. 2 also shows the point 16 with the highest energy dose that is generated at approximately 100 g/m$^2$ by electron accelerator 3a. The electron reflectors 7a1 and 7a2 are arranged at approximately this point. Taking into account the weight per unit area shown as shaded area 15 of the electron exit window 5a of approximately 50 g/m$^2$, in air the optimal distance of the reflectors 7a1 and 7a2 from the electron exit window 5a results of approximately 42 mm. The same ratios apply for the electron accelerator 3b with reflectors 7b1 and 7b2.

FIG. 3 shows a detailed view of a reflector system, comprising the reflectors 7a1 and 7b1 from FIG. 1, which at the same time are embodied as component parts of a sensor system. It can be seen from FIG. 3 that the reflectors 7a1 and 7b1 are subdivided in the y direction, that is in the direction of movement of the article 2, into partial reflectors 7a1.1 and 7a1.2 or 7b1.1 and 7b1.2. Each partial reflector is thereby arranged electrically insulated with respect to all of the other partial reflectors. Thus as a measuring device 9a1.1 is assigned to the partial reflector 7a1.1, a measuring device is also assigned to every other partial reflector, by means of which measuring device the electron currents striking the assigned partial reflector can be detected.

As described above with respect to reflectors 7a1 and 7b1, the reflectors 7a2 and 7b2 arranged in a mirror symmetrical manner to the reflectors 7a1 and 7b1 are also subdivided into partial reflectors, which at the same time with associated measuring devices are component parts of a sensor system.

In this manner there are at least two measuring points with corresponding measurement results respectively in the x, y and z direction, by means of which results a statement is thus possible regarding the electron current density distribution in the x, y and z direction. It should be discernible thereby that a more precise statement can be made regarding the electron current density distribution, the higher the number of the partial reflectors embodied in the x, y and/or z direction.

Depending on the electron current density distributions determined in this manner, device 1 is therefore suitable for the continuous process control by monitoring and optionally controlling the beam current density distribution of the two electron accelerators 3a and 3b lying opposite one another. By means of the device 1 according to the invention it is therefore possible on the one hand to bombard with electrons in a surface-covering manner the entire surface of an article 2 despite only two electron exit windows 5a, 5b, on the other hand, the operation can be controlled thereby such that all of the surface sections are bombarded with a largely uniform energy dose.

Through the combination of reflector system and sensor system it is furthermore possible to monitor the stay of the articles 2 in the process zone in terms of space and time. With the absence of an article 2, the edge beams 8 strike the respectively opposite reflector (e.g., edge beam 8a1 strikes reflector 7a1 and then reflector 7a2) and are registered in the sensor system as an ascending electron current value. With the presence of an article 2 in the process zone, the article 2 however absorbs the reflected edge beams and the registered signal is reduced. In addition the proportion of other scattered electrons that strike the sensor system is reduced. A statement can thus be made on whether a article 2 is located in the process chamber.

The invention claimed is:

1. A device for altering characteristics of a three-dimensional article using electrons, said device comprising:
at least one electron accelerator for generating accelerated electrons;
two and only two electron exit windows;
the two electron exit windows being constructed and arranged opposite one another;
at least one electron reflector;
the two electron exit windows and the at least one electron reflector delimiting a process chamber;
within said chamber a surface or surface layer of the three-dimensional article is bombarded with electrons, wherein by means of a sensor system which measures an electron current striking the at least one electron reflector an energy density distribution inside the process chamber can be detected at least over one spatial dimension.

2. A device according to claim 1, wherein:
each of the electron exit windows has a flat surface.

3. A device according to claim 1, wherein:
the electron exit windows have respective surfaces aligned parallel to one another.

4. A device according to claim 1, wherein:
the electron exit windows have respective surfaces positioned at an angle to one another.

5. A device according to claim 1, wherein:
at least one of said electron exit windows has a window having a concave surface facing toward the process chamber so as to face the article.

6. A device according to claim 1, wherein:
at least one of said electron exit windows has a surface adapted to a geometry of the article.

7. A device according to claim 1, wherein:
one of said at least one electron accelerator for generating accelerated electrons comprises a controlling device to control electron energy density emitted over the area of at least one electron exit window such that different electron energy densities are emitted over individual partial areas of said one electron exit window.

8. A device according to claim 1, wherein:
said at least one reflector comprises at least two reflectors arranged in a mirror symmetrical manner on opposite sides of the process chamber.

9. A device according to claim 8, wherein:
said at least two reflectors are component parts of a sensor system for detecting an energy density distribution inside the process chamber.

10. A device according to claim 9, wherein:
said sensor system for detecting an energy density distribution comprises a sensor system for detecting an electric voltage with respect to an electric mass or other electric potential on said at least two reflectors or partial reflectors.

11. A device according to claim 9, wherein:
said sensor system for detecting an energy density distribution comprises a sensor system for detecting said energy density distribution in an x, y and/or z direction of a Cartesian coordinate system.

12. A device according to claim 1, wherein:
at least one of said electron exit windows are structured and arranged to be moved depending on a geometry of the article and/or a position of the article between the electron exit windows.

13. A device according to claim 1, wherein:
at least one of said electron exit windows is embodied as a vacuum-tight film.

14. A device according to claim 1, wherein:
at least one of said electron exit windows is embodied as a gas-permeable pressure stage arrangement between electron accelerator and process chamber.

15. A device according to claim 1, further comprising:
a sensor system for adjusting power of the electron accelerator for generating accelerated electrons to a process-specific value, depending on whether an article is located in the process chamber.

16. A device according to claim 1, further comprising:
a controlling device to control an exit direction of an electron from at least one of said two electron exit windows.

17. A device according to claim 1, wherein:
the at least one electron accelerator is embodied as a band emitter or as an axial beam generator.

18. A device according to claim 1, wherein:
each of the electron exit windows includes a film; and
the two electron exit windows have a spacing within a range according to the following equation:

$$a = f * \frac{6{,}67 * 10^{-7} \frac{(Ub * k_1)^{5/3}}{\rho_W} * k_2 - \rho_F * d_F}{\rho_G}$$

whereby,
$U_b$=acceleration voltage
$\rho_W$=density of water
$\rho_G$=density of the medium between the electron exit windows
$\rho_F$=density of the window film
$d_F$=thickness of the window film
$k_1 = 1 * V^{-1}$
$k_2 = 1 * (g/m^2)^{-1}$
with a spacing factor f(0.5<f<1.5).

19. A method for altering characteristics of a three-dimensional article using electrons, said method comprising:
generating electrons, accelerating said electrons, and emitting said electrons over a surface of two opposite electron exit windows, and only two electron exit windows, by means of at least one electron accelerator;
bombarding a surface or surface layer of the article with said electrons while said article is within a process chamber delimited by the two opposite electron exit windows and at least one electron reflector;
detecting by means of a sensor system, over at least one spatial dimension, an energy density distribution inside the process chamber;
measuring an electron current striking the at least one reflector with the sensor system, and
having a spacing of the electron exit windows adjusted such that an influence of one of the electron exit windows by emitted energy of an oppositely positioned electron exit window is negligible.

20. A method according to claim 19, wherein:
the spacing of the electron exit windows is adjusted dependent upon acceleration voltage of said emitted electrons and thickness and density of the electron exit windows.

21. A method according to claim 20, wherein:
each of the electron exit windows includes a film; and
the spacing of the electron exit windows is adjusted to be in a range according to the following equation:

$$a = f * \frac{6{,}67 * 10^{-7} \frac{(Ub * k_1)^{5/3}}{\rho_W} * k_2 - \rho_F * d_F}{\rho_G}$$

whereby,
a=spacing of the electron exit windows
$U_b$=acceleration voltage
$\rho_W$=density of water
$\rho_G$=density of the medium between the electron exit windows
$\rho_F$=density of the window film
$d_F$=thickness of the window film
$k_1 = 1 * V^{-1}$
$k_2 = 1 * (g/m^2)^{-1}$
with a spacing factor f(0.5<f<1.5).

22. A method according to claim 19, further comprising:
guiding the article through the process chamber at a constant speed during said bombarding with electrons.

23. A method according to claim 19, further comprising:
guiding the article into the process chamber; and
the bombarding comprises bombarding the article in the process chamber with electrons in a stationary state by a one-time or multiple irradiation operation.

24. A method according to claim 19, wherein:
the bombarding comprises bombarding a surface or surface layer of the article in the process chamber with electrons in a step-and-repeat mode.

25. A method according to claim 19, further comprising:
rotating the article in the process chamber around an axis extending between the two electron exit windows; and
during said rotating, bombarding the article with electrons by a one-time or multiple irradiation operation.

26. A use of a method according to claim 19, wherein:
said method is used for altering characteristics of parts in at least one of the following: plastics; sterilizing products/intermediate products of the pharmaceutical industry;
disinfecting and/or sterilizing packaging, hardening coatings or disinfecting and/or sterilizing objects, fruits, or other natural products.

27. A device for altering characteristics of a three-dimensional article using electrons, said device comprising:
at least one electron accelerator for generating accelerated electrons;
two electron exit windows;
the two electron exit windows being constructed and arranged opposite one another;
at least one electron reflector;
the two electron exit windows and the at least one electron reflector delimiting a process chamber;
within said chamber the surface or surface layer of the three-dimensional article is bombarded with electrons, wherein by means of a sensor system an electron current striking the at least one electron reflector is measured and an energy density distribution inside the process chamber can be detected at least over one spatial dimension;

the two electron exit windows have a spacing within a range according to the following equation:

$$a = f * \frac{6{,}67 * 10^{-7} \frac{(Ub * k_1)^{5/3}}{\rho_W} * k_2 - \rho_F * d_F}{\rho_G}$$

whereby,
$U_b$=acceleration voltage
$\rho_W$=density of water
$\rho_G$=density of the medium between the electron exit windows
$\rho_F$=density of the window film
$d_F$=thickness of the window film
$k_1=1*V^{-1}$
$k_2=1*(g/m^2)^{-1}$
f=spacing factor f(0.5<f<1.5).

28. A method for altering characteristics of a three-dimensional article using electrons, said method comprising:
generating electrons, accelerating said electrons, and emitting said electrons over a surface of two opposite electron exit windows by means of at least one electron accelerator, each of the electron exit windows including a film;
bombarding a surface or surface layer of the article with said electrons while said article is within a process chamber delimited by the two opposite electron exit windows and at least one electron reflector;
detecting by means of a sensor system, over at least one spatial dimension, an energy density distribution inside the process chamber;
measuring an electron current striking the at least one reflector with the sensor system, and
having a spacing of the electron exit windows adjusted such that an influence of one of the electron exit windows by emitted energy of an oppositely positioned electron exit window is negligible;
the spacing of the electron exit windows being adjusted within a range, dependent upon acceleration voltage of said emitted electrons and thickness and density of the electron exit windows, according to the following equation:

$$a = f * \frac{6{,}67 * 10^{-7} \frac{(Ub * k_1)^{5/3}}{\rho_W} * k_2 - \rho_F * d_F}{\rho_G}$$

whereby,
a=spacing of the electron exit accelerators
$U_b$=acceleration voltage
$\rho_W$=density of water
$\rho_G$=density of the medium between the electron exit windows
$\rho_F$=density of the window film
$d_F$=thickness of the window film
$k_1=1*V^{-1}$
$k_2=1*(g/m^2)^{-1}$
with a spacing factor f(0.5<f<1.5).

29. A device according to claim 1, wherein:
the at least one electron reflector comprises:
a first portion that redirects electrons from one of the two and only two electron exit windows toward a side surface or surface layer of said article, and
a second portion that redirects electrons from the other of the two and only two electron exit windows toward a side surface or surface layer of said article.

30. A device according to claim 1, wherein:
the at least one electron reflector comprises two oppositely arranged electron reflectors each having:
a first portion that redirects electrons from one of the two and only two electron exit windows toward a side surface or surface layer of said article, and
a second portion that redirects electrons from the other of the two and only two electron exit windows toward a side surface or surface layer of said article.

* * * * *